(12) United States Patent
Rooks et al.

(10) Patent No.: US 8,083,737 B2
(45) Date of Patent: Dec. 27, 2011

(54) GAS-ENHANCED SURGICAL INSTRUMENT WITH MECHANISM FOR CYLINDER PUNCTURE

(75) Inventors: Kathy E. Rooks, Boulder, CO (US); Russell Hempstead, Lafayette, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 189 days.

(21) Appl. No.: 12/548,049

(22) Filed: Aug. 26, 2009

(65) Prior Publication Data

US 2011/0054454 A1    Mar. 3, 2011

(51) Int. Cl.
*A61B 18/14*    (2006.01)
(52) U.S. Cl. .............. 606/41; 606/45; 606/49
(58) Field of Classification Search .......... 606/41, 606/49; 604/23–26; 141/119, 329
See application file for complete search history.

(56) References Cited

U.S. PATENT DOCUMENTS

| | | | |
|---|---|---|---|
| 3,688,765 A * | 9/1972 | Gasaway | 604/70 |
| 5,330,469 A | 7/1994 | Fleenor | |
| 5,669,904 A | 9/1997 | Platt, Jr. et al. | |
| 5,669,907 A | 9/1997 | Platt, Jr. et al. | |
| 5,720,745 A | 2/1998 | Farin et al. | |
| 5,732,752 A * | 3/1998 | Glessner et al. | 141/329 |
| 5,957,162 A * | 9/1999 | Arai | 138/31 |
| 6,210,369 B1 * | 4/2001 | Wilmot et al. | 604/157 |
| 6,213,999 B1 | 4/2001 | Platt, Jr. et al. | |
| 6,740,081 B2 | 5/2004 | Hilal | |
| 6,958,063 B1 | 10/2005 | Soll et al. | |
| 2004/0044342 A1 | 3/2004 | Mackay | |
| 2006/0052771 A1 | 3/2006 | Sartor et al. | |
| 2006/0052772 A1 * | 3/2006 | Sartor et al. | 606/41 |
| 2006/0200122 A1 | 9/2006 | Sartor et al. | |
| 2009/0048594 A1 | 2/2009 | Sartor | |

FOREIGN PATENT DOCUMENTS

| | | |
|---|---|---|
| EP | 1561430 | 10/2005 |
| WO | WO 9305721 | 4/1993 |
| WO | 2005016142 | 2/2005 |

OTHER PUBLICATIONS

"Technology of Argon Plasma Coagulation with Particular Regard to Endoscopic Applications", Endoscopic Surgery and Allied Technologies, No. 1, vol. 2, Feb. 1994.
International Search Report EP10174107 dated Nov. 5, 2010.

* cited by examiner

*Primary Examiner* — Michael Peffley
*Assistant Examiner* — Samantha Good

(57) ABSTRACT

A surgical instrument for providing an ionized gas to a surgical site includes a receptacle for a cylinder of pressurized surgical gas and a frame having a port near the distal end for emitting the surgical gas. A passageway extending between the receptacle and the port delivers the surgical gas to an electrode that is adapted for connection to a source of electrosurgical energy. A puncture assembly for rupturing a seal on the cylinder to release the surgical gas into the passageway includes a spring movable between a first state for storing mechanical energy and a relaxed state. An actuator is operable to move the spring to the relaxed state. A puncture pin is operatively coupled to the spring such that energy released by movement of the spring to the relaxed state is effective to move the puncture pin relative to the cylinder to rupture the seal.

13 Claims, 8 Drawing Sheets

GAS-ENHANCED SURGICAL INSTRUMENT WITH MECHANISM FOR CYLINDER PUNCTURE

BACKGROUND

1. Technical Field

The present disclosure relates to an apparatus for surgically treating tissue with a pressurized gas. In particular, the disclosure relates to an apparatus with a mechanism for releasing the gas from a cylinder or tank.

2. Background of Related Art

Surgical instruments are commonly used for procedures such as tissue division, dissection, ablation, coagulating and arresting blood loss in tissue. One type of instrument employs a heated probe to arrest bleeding in a technique called thermic coagulation. Heat may be conducted from a relatively hot probe tip to the tissue to be treated by moving the probe into contact or into close proximity with the tissue. The probe may adhere to the tissue while the tissue is being treated, and thus removing the probe often causes repeat bleeding. Many such probes also produce an undesirable buildup of eschar on or proximate the tip, which detrimentally affects the efficiency of the surgical instrument. Another type of instrument directs high frequency electric current through the tissue to stop bleeding. These instruments typically include at least one electrode for contacting the tissue to be treated to establish electrical communication with the tissue. Again, tissue adherence and eschar buildup may occur with these instruments.

Other instruments achieve coagulation by providing a gas to the atmosphere adjacent the targeted tissue. An ionizable gas, for example argon gas, may be directed toward the tissue past an electrode just prior to exiting a distal end of the instrument. An electrosurgical current may be conducted to the tissue through ionized conductive pathways in the gas without requiring direct contact between the electrode and the tissue. Providing an atmosphere of ionized gas may also be beneficial, for example, since the gas displaces oxygen from the area and reduces oxidative stress of the tissue.

The gas may be held in pressurized cylinders or tanks until a surgeon is ready to begin treatment Relatively large cylinders may be fixed in one location or may be disposed on a movable cart in the operating room. A gas supply hose fluidly connects the remote cylinders to the instrument. Other configurations provide for a relatively small cylinder to be housed within a receptacle defined in a hand-held instrument. In either case, a seal in the cylinder may be ruptured to initiate the flow of the gas to the instrument. A substantial force, about 60 lbs in some instances, may be required to rupture the cylinder seal. Providing such a force may be difficult or distracting for a surgeon or support clinician in an operating environment.

SUMMARY

The present disclosure describes a surgical instrument for providing a gas to a surgical site. The instrument includes a receptacle for receiving a cylinder of pressurized surgical gas, and a flame having a port near a distal end for emitting the surgical gas. An electrode disposed adjacent the distal end of the flame is connected to a source of electrosurgical energy, and a passageway extends between the receptacle and the port to deliver the surgical gas to the electrode. A puncture assembly is provided for rupturing a seal defined by the cylinder to release the surgical gas into the passageway. The puncture assembly includes a spring movable between a first state for storing mechanical energy and a relaxed state, and an actuator operable to move the spring to the relaxed state. A puncture pin is operatively coupled to the spring such that energy released by movement of the spring to the relaxed state is effective to move the puncture pin relative to the cylinder to rupture the seal.

The puncture pin may be operatively coupled to the spring with a gear rack and a pinion gear such that movement of the spring to the relaxed state induces longitudinal motion in the gear rack, and longitudinal motion in the gear rack induces rotational motion in the pinion gear. Also, the pinion gear may be operatively coupled to a cam shaft such that rotational motion in the cam shaft induces longitudinal motion between the puncture pin and the cylinder. The actuator may include a plunger configured to engage a slot in the cam shaft such that disengaging the plunger from the slot induces movement of the spring to the relaxed state.

The receptacle may be configured to receive a plurality of cylinders and the cam shaft may operatively engage a plurality of puncture pins such that each puncture pin is movable relative to a respective cylinder. The puncture pins may each move simultaneously with respect to one another relative to the respective cylinder such that each of the cylinders is punctured simultaneously. Alternatively, puncture pins may each move sequentially with respect to one another relative to a respective cylinder such that each of the cylinders is punctured sequentially. The cam shaft may include a radially offset cam surfaces such that each of cam surfaces operatively engages a respective puncture pin to puncture the cylinders sequentially.

The at least one spring may include a compression spring subject to a compressive force in the first state. Alternatively, the at least one spring may include an extension spring subject to a tensile force when in the first state.

The surgical instrument may be configured such that the receptacle is disposed within the frame. Alternatively, the receptacle may be disposed remotely with respect to the flame, and the passageway may include a gas supply hose fluidly connecting the receptacle with the frame.

The surgical instrument may be configured such that the source of electrosurgical energy is disposed within the frame. Alternatively, the source of electrosurgical energy may be remotely coupled to the frame by a cable.

According to another aspect of the disclosure, a surgical instrument for providing a surgical gas to a surgical site includes a receptacle for receiving a cylinder of pressurized surgical gas and a frame defining a port near a distal end for emitting the surgical gas. A passageway extending between the receptacle and the port defined in the frame. A puncture assembly is provided for rupturing the cylinder to release the surgical gas into the passageway. The puncture assembly includes a bank for storing mechanical energy, an actuator responsive to an actuation force to release the mechanical energy from the bank, and a puncture pin operatively coupled to the bank such that the release of energy from the bank moves the puncture pin relative to the cylinder with a puncture force greater than the actuation force. The bank may include at least one spring movable between a compressed state for storing mechanical energy and a relaxed state.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1A:
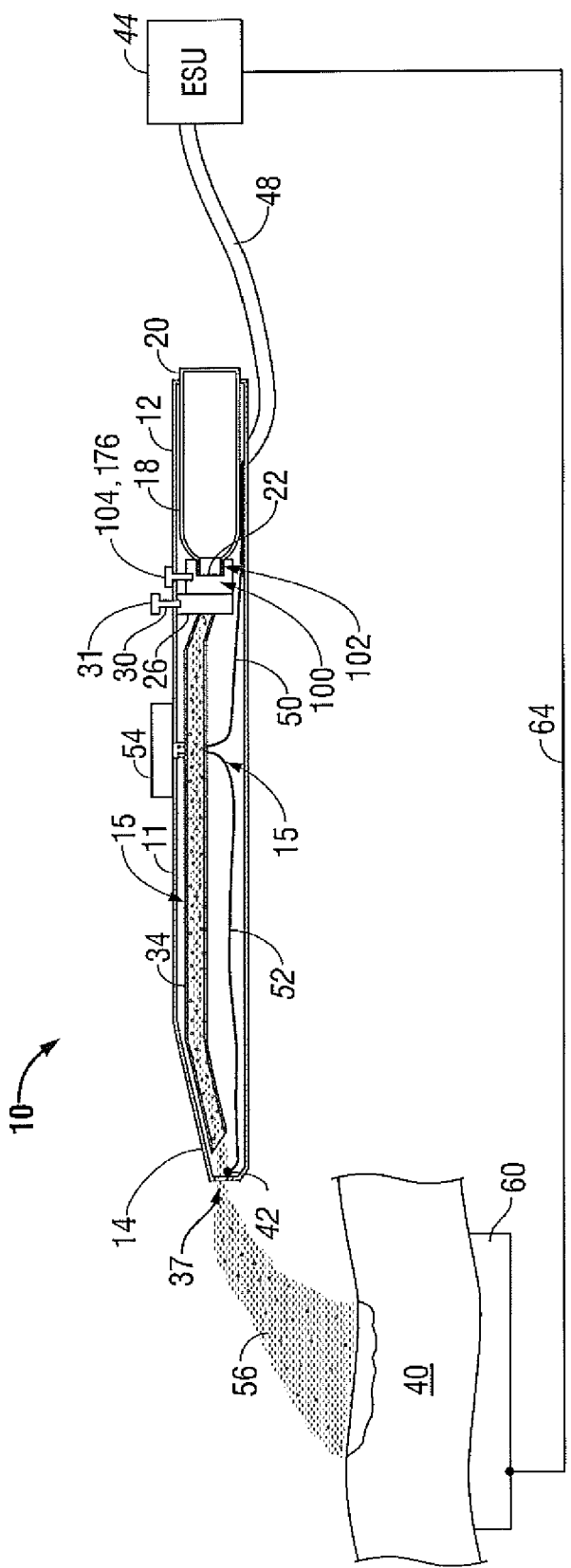
FIG. 1A is a schematic view of an electrosurgical coagulator according to the present disclosure depicting a gas cylinder and puncture assembly incorporated into a hand-held applicator.

Referring initially to FIG. 1A, an embodiment of an electrosurgical instrument is depicted generally as 10. The instrument 10 is dimensioned to resemble a pencil for hand-held or robotic manipulation for use in open surgical procedures. However, it is envisioned that a similar instrument may be configured, for example, with a pistol grip or other handle for use in laparoscopic or endoseopic surgical procedures. Further, although the basic operating features of instrument 10 are described herein in connection to an open surgical procedure, the same or similar operating features may be employed in connection with a laparoscopic or endoscopic procedure without departing from the scope of the present disclosure. The term "electrosurgical energy" herein refers to any type of electrical energy which may be utilized for medical procedures. The term "proximal," as is traditional, herein refers to the end of instrument 10 (or other element) which is closer to a user, while the term "distal" will refer to the end which is further from the user.

Instrument 10 includes an elongated housing 11 having a proximal end 12, a distal end 14 and an elongated cavity 15 extending therethrough. The housing 11 defines a receptacle 18 near the proximal end 12 for receiving a gas container, canister, cartridge or cylinder 20. Cylinder 20 contains a surgical gas, e.g., a noble or inert gas such as argon, or mixture of noble or inert gases. Cylinder 20 is relatively small, single-use and disposable. A rupture disk seal 22 at a forward end of the cylinder 20 exhibits a sufficient strength to maintain the required gas pressure in the cylinder 20. A gas pressure of about 3000 psi or less and a compressed gas volume of about 100 cubic centimeters or less have been found suitable for some coagulation procedures. To effectively contain the gas, rupture disk 22 may be constructed of a thin metal sheet such as stainless steel or beryllium copper.

The forward end of cylinder 20 is received by a puncture assembly 100. Puncture assembly 100 includes a threaded point 102 to positively engage the forward end of cylinder 20. Alternatively, the use of spring clips, bayonet locks, friction fit or similar engagement arrangements are also contemplated. Puncture assembly 100 includes a release pin 104 extending to an exterior of the housing 11 such that the release pin 104 is accessible to a user during a coagulation procedure. Release pin 104 is operable to selectively puncture rupture disk 22 and release the gas from cylinder 20 as described in greater detail below with reference to FIGS. 3 through 6. In other embodiments, the release pin 104 may be eliminated, and a plunger screw 176 may serve as a controlling feature to actuate a puncture assembly. Examples of such embodiments are described below with reference to FIGS. 7 through 8B.

Adjacent puncture assembly 100 is a plenum 26, which receives the surgical gas once rupture disk 22 is punctured. Plenum 26 communicates with a regulator or valve 30 such that a flow rate of the surgical gas through the instrument 10 may be controlled. Regulator or valve 30 includes an actuator 31 projecting outside the housing 11 to facilitate operation by a user during a coagulation procedure. In fluid communication with the regulator or valve 30 is a gas supply tube 34, which extends generally longitudinally through housing 11 to the distal end 14. Gas supply tube 34 terminates proximally of a distal port 37 defined at the distal end 14 of the housing 11. The distal port 37 is configured to emit, expel or disperse the surgical gas emanating from the gas supply tube 34 toward targeted tissue 40 at a surgical site. Distal port 37 may be configured to promote gas flow in a uniform and consistent manner, or alternatively in a more turbulent manner.

The housing 11 supports an electrode 42 between the gas supply tube 34 and the distal port 37. Surgical gas emanating from the gas supply tube 34 is ionized by the electrode 42 before exiting the housing 11 through the distal port 37. The electrode 42 may alternatively be disposed on the exterior of housing 11 near the distal port 37 such that surgical gas emanating from the distal port 37 is ionized. The electrode 42 is configured as a substantially spherical member, but may alternatively be configured as a blade, needle or snare and may be suitable for fulguration, coagulation, cutting or sealing tissue.

A source of electrosurgical energy, generally designated "ESP," supplies electrode 42 with the electrosurgical energy to ionize the surgical gas. An electrosurgical generator 44 serves to produce the electrosurgical energy and also to control and monitor the delivery of the electrosurgical energy. Various types of electrosurgical generators 44, such as those generators provided by Energy-based Devices, a global business unit, of Covidien, of Boulder, Colo., may be suitable for this purpose. Electrosurgical generator 44 is electrically and mechanically coupled to the proximal end of housing 11 by a cable 48, which electrically communicates with a pair of leads 50, 52 on the interior of the housing 11. The two leads 50, 52 are coupled to an actuator such as button trigger 54. Trigger 54 is mounted on an accessible top side of housing 11, and is operable to selectively initiate and terminate the delivery of electrossurgical energy from the electrosurgical generator 44. Button trigger 54 may alternatively be configured as any other type of known actuator, e.g., a rocker switch, dial, slide switch, etc. When the trigger 54 is appropriately actuated, electrosurgical energy is delivered to the electrode 42.

Figure 1B:
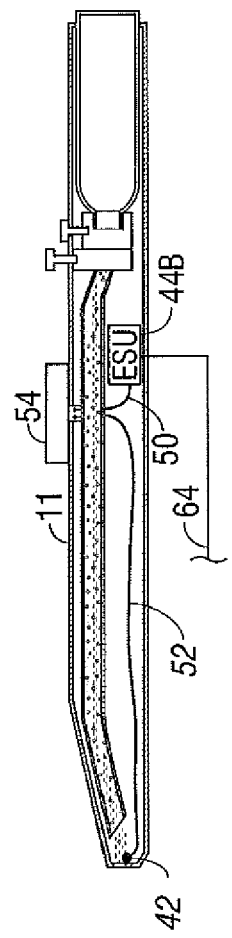
FIG. 1B is a schematic view of an alternate embodiment of the hand-held applicator of FIG. 1A including an electrosurgical generator incorporated therein.

In an alternate embodiment depicted in FIG. 1B, an electrosurgical generator 44B is adapted to be supported within the housing 11. By providing a source of electrosurgical energy within housing 11, the cable 48 (FIG. 1A) may be eliminated making the instrument less cumbersome to operate in some instances.

As indicated above the surgical gas emanating from the distal port 37 may be ionized by the electrode 42 when the electrode 42 is appropriately supplied with electrosurgical energy. The ionized gas forms plasma 56, which provides an electrical pathway between the electrode 42 and the tissue 40 to be treated. Thus, electrosurgical energy may be conducted to the tissue 40 without physical contact with the electrode 42 or housing 11.

As is common in monopolar electrosurgical systems, a return electrode or return pad 60 is positioned under the tissue 40 or generally under a patient. The return pad 60 is coupled to the electrosurgical generator 44 by a cable 64. Cable 64 is, in turn, coupled to an appropriate electrical potential provided by the generator 44 such that return pad 60 provides an electrical return for the electrosurgical energy.

Figure 2:
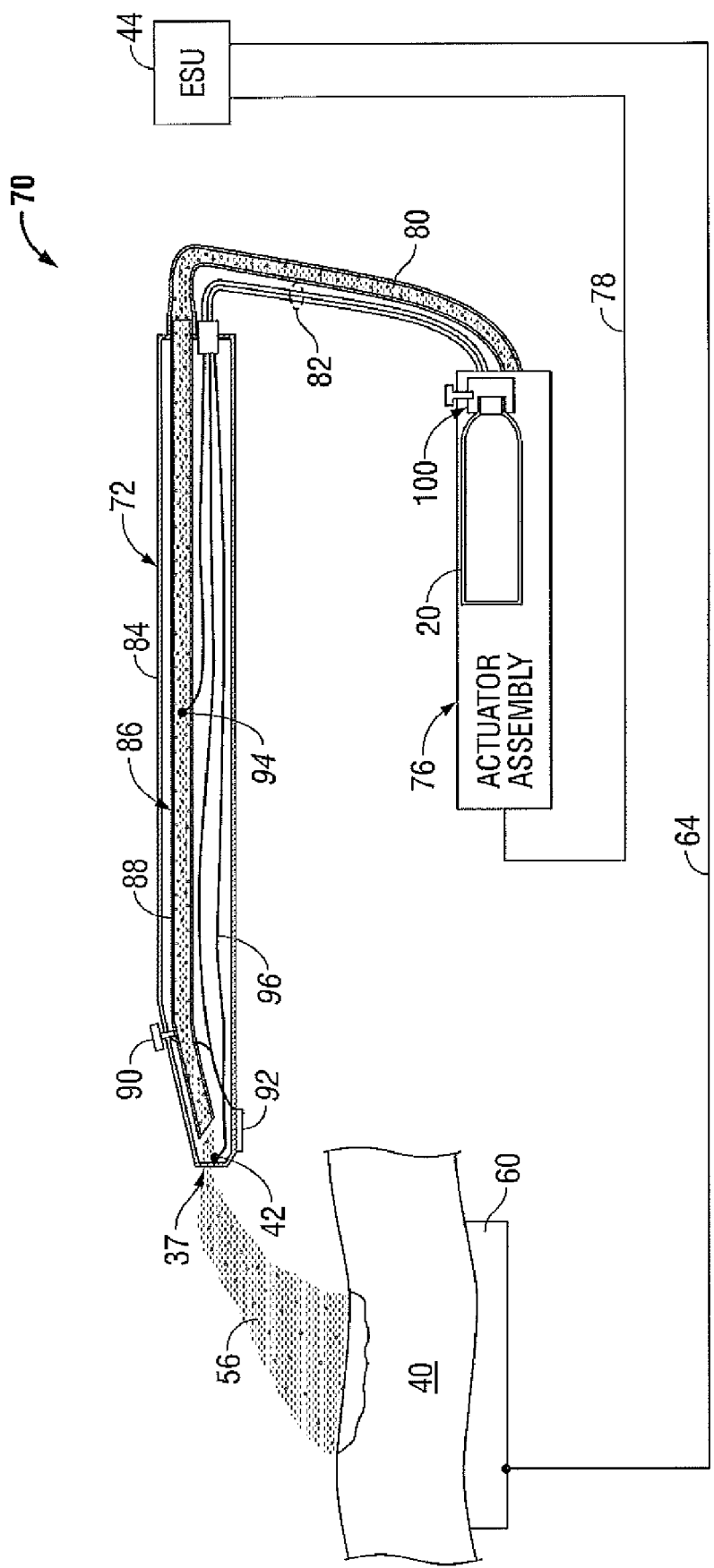
FIG. 2 is a schematic view of an alternate embodiment an electrosurgical coagulator in accordance with the present disclosure depicting the gas cylinder and puncture assembly disposed remotely with respect to a hand held applicator.

Referring now to FIG. 2, an alternate embodiment of an electrosurgical instrument is depicted generally as 70. Electrosurgical instrument 70 includes a hand-held applicator 72 and a remote actuator assembly 76. The remote actuator assembly 76 includes one or more cylinders 20 containing a surgical gas, and puncture assembly 100 for releasing the surgical gas. Providing a remote actuator assembly 76 permits the use of a larger gas supply than may conveniently be accommodated in the hand-held applicator, thus facilitating prolonged use of the instrument 70. The remote actuator assembly 76 may include an actuator such as a foot switch, hand-held trigger, or other device that is operable to selectively initiate and terminate the delivery of electrosurgical energy from the electrosurgical generator 44.

The actuator assembly 76 is coupled to the electrosurgical generator 44 by an electrical cable 78. The actuator assembly 76 may be positioned near the generator 44 such that actuator assembly 76 and the generator 44 may be conveniently operated by a nurse or other support personnel. The actuator assembly 76 is coupled to the hand-held applicator 72 by a gas supply hose 80 for the delivery of the surgical gas and an electrical cable 82 for communicating electrosurgical energy, instructions and data.

The hand-held applicator 72 includes an elongated housing 84 and an elongated cavity 86 extending therethrough. Extending through the housing 84 is a gas delivery tube 88 for transmitting the surgical gas between the gas supply hose 80 and the electrode 42. A distal point 37 directs the surgical gas or plasma 56 toward the tissue 40 to be treated as described above with reference to FIG. 1A. A return pad 60 and cable 64 provide a return path to the generator 44 for electrosurgical energy.

The hand held applicator includes a single actuator 90, which is associated with a valve or regulator to control the flow of surgical gas. The actuator 90 extends to an accessible exterior of the housing 84 to facilitate manipulation by a surgeon. It is also contemplated that actuator assembly 90 may cooperate with one or more sensors 92, 94 positioned near the distal poll 37 and within the supply tube 88 respectively. Sensor 92 is configured to continually measure or monitor a condition in the vicinity of the tissue 40 to be treated, e.g., the amount of tissue coagulation, and relay the information to generator 44 through leads 96 and cables 82, 78. Generator 44 may include a control system or safety circuit (not shown) in communication with the actuator 90 such that the actuator 90 may be controlled by the generator 44 in response to a condition sensed by sensor 92. Similarly, sensor 94 may be employed to measure a pressure or flow rate of surgical gas in the supply tube 88, and relay the information to the generator 44.

Various additional and alternative aspects of the construction and use of a gas enhanced surgical instrument 10, 70 may be employed to facilitate the treatment of tissue 40. Many of these aspects are discussed in commonly-owned U.S. Provisional application Ser. No. 12/240,252 bearing the publication No. 2009/0054893.

Figure 3:
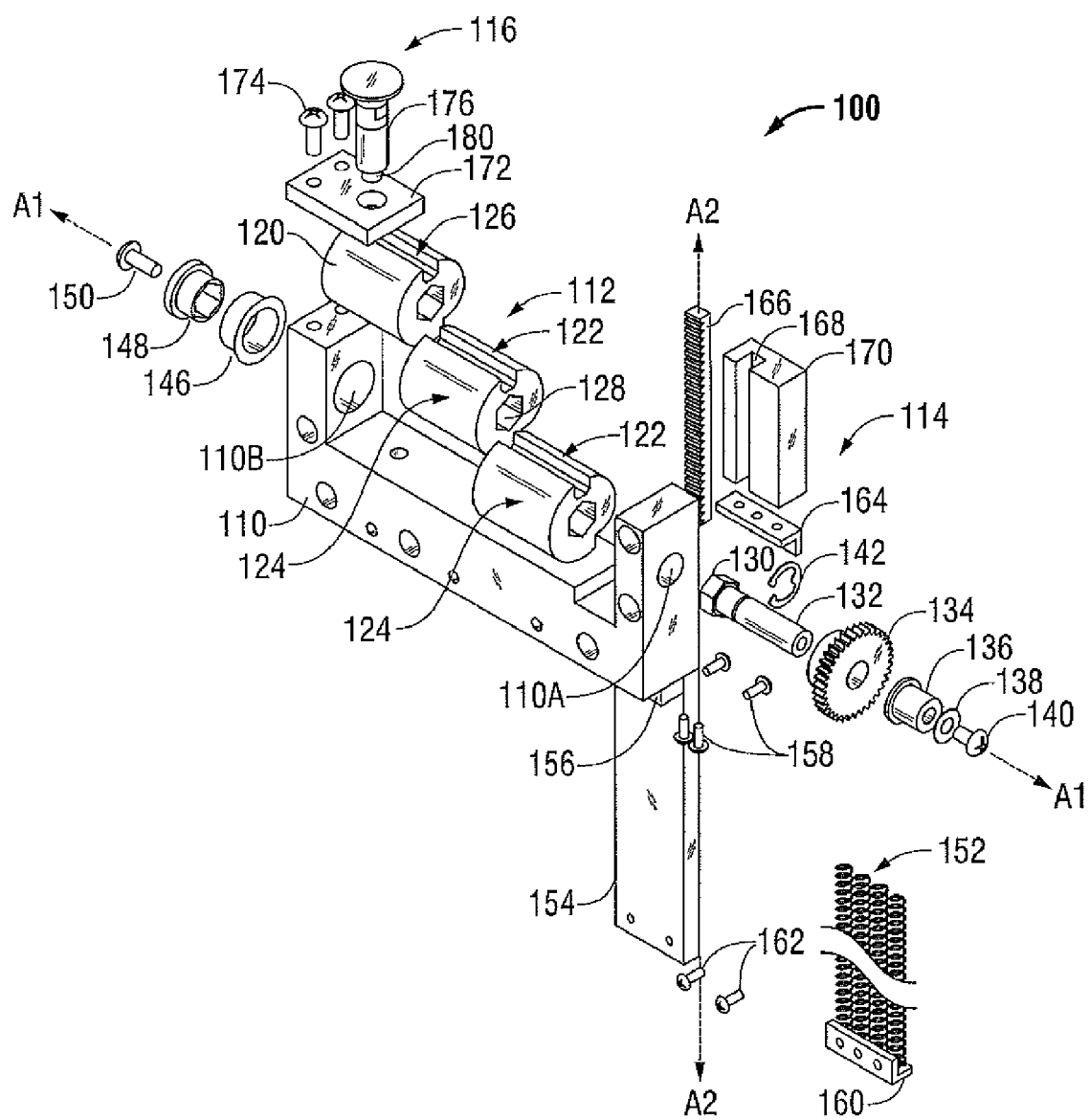
FIG. 3 is an exploded, perspective view of the puncture assembly of FIGS. 1 and 2.
Figure 4:
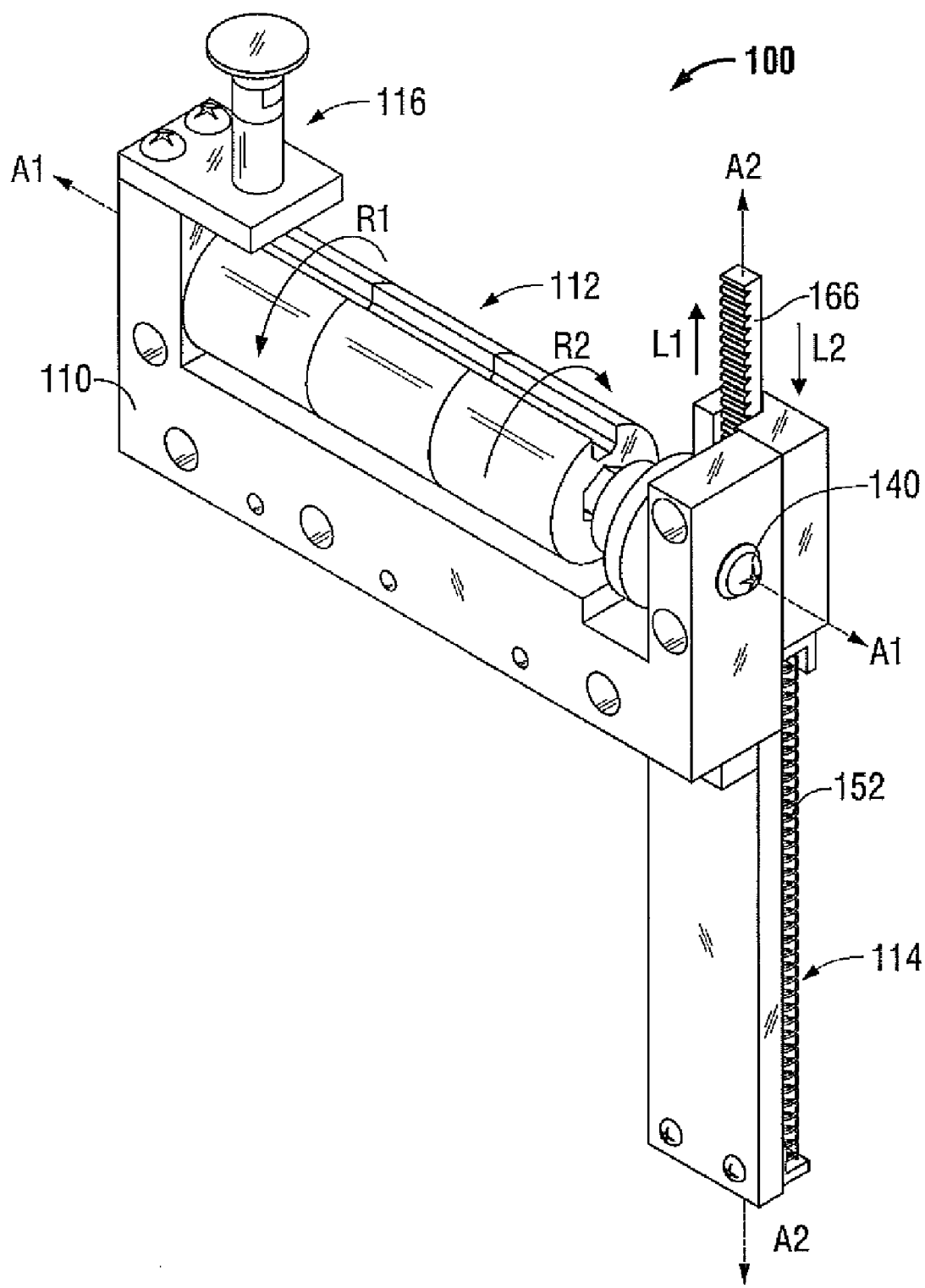
FIG. 4 is a perspective view of the puncture assembly in an assembled configuration.

Referring now to FIGS. 3 and 4, puncture assembly 100 may be employed to breach the rupture disk 22 (FIG. 1A) of a gas cylinder 20. The puncture assembly 100 includes a frame 110, which provides a mounting structure for various other components of the puncture assembly 100. Generally, the frame 110 supports a cam shaft 112, a spring drive assembly 114 and a plunger assembly 116. The cam shaft 112 is mounted in a rotatable manner about a first axis A1, and the spring drive assembly is mounted to support longitudinal motion about a second axis A2.

The cam shaft 112 includes three drum members 120. Each drum includes a circumferential cam surface 122 and a neutral surface 124. The cam surfaces 122 are sloped such that a radius of the respective drum member 120 increases along the cam surface 122 while the neutral surfaces exhibit a constant radius. A longitudinal slot 126 extends along the drum members 120 and separates the cam and neutral surfaces 122, 124. The drum members 120 also include a hexagonal drive bore 128 extending longitudinally therethrough. The drive bore of one of the drum members is engaged by a head 130 of a hexagonal drive key 132 such that the drum member 120 rotates along with the drive key 132. Each of the drum members 120 may be coupled to adjacent drum members 120 by a coupling member (not shown) having a head similar to head 130 of drive key 132 such that each of the drum members rotates together. Similarly, the drive key 132 is engaged by a pinion gear 134 such that the drive key 132 rotates with the pinion gear 134.

The frame 110 defines first and second bores 1110a and 110b for supporting the cam shaft 112. A flanged bushing 136 is press fit into the first bore 110a and receives the drive key 132 such that the drive key 132 is free to rotate therein. The drive key 132 is longitudinally secured in the frame 110 with a washer 138 and screw 140 on one side of the bore 110a and an E-ring on an opposite side of the bore 110a. The pinion gear 134 is secured to the drive key 132 between the bushing 136 and the E-ring 142. A flanged bushing 146 is press fit into the second bore 110b. The bushing 146 receives a hexagonal cap 148 such that the hexagonal cap 148 is free to rotate therein. A screw 150 secures the hexagonal cap 148 to a drum member 120 via a coupling member (not shown) having a head that extends into an interior portion the hexagonal cap 148. This arrangement permits each drum member 120, the drive key 132, pinion gear 134 and hexagonal cap 148 of the cam shaft 112 to rotate together. In other embodiments, a cam shaft (not shown) may be configured such that each drum member 120 rotates independently or in another arrangement to facilitate the puncture of multiple cylinders.

Rotation in the cam shaft 112 may be induced by operation of the spring drive assembly 114. The drive assembly 114 includes a bank of four compression springs 152, which, in combination, have the capacity to store sufficient energy to permit the puncture assembly 100 to puncture at least one rupture disk seal 22 (FIG. 1A). In alternative embodiments, including the embodiment discussed below with reference to FIGS. 8A and 8B, sufficient energy may also be stored by springs in an elongated or tensile state.

The drive assembly 114 includes an elongate support plate 154 fixedly mounted to the frame 110 by a coupling member 156 and screws 158. The springs 152 are supported on a first L-bracket 160 that is fixedly mounted to the elongate support plate 154 with screws 162. A second L-bracket 164 opposes the first L-bracket 160 and engages the springs 152 such that the second L-bracket 164 is longitudinally movable in the direction of the second axis A2. The longitudinal position of the second L-bracket 164 depends on the degree of compression in the springs 152. A gear rack 166 is fixedly coupled to the second L-bracket 164 such that the gear rack 166 moves longitudinally with the second L-bracket 164. The gear rack 166 moves longitudinally within a slot 168 defined in a rack placement bracket 170. The rack placement bracket 170 is fixedly coupled to the frame 110.

The gear rack 166 of the drive assembly 114 engages the pinion gear 134 of the cam shaft 112 such that longitudinal motion in the drive assembly 114 induces rotational motion in the cam shaft 112. Longitudinal movement of the gear rack 166 in the direction of arrow L1 induces rotational motion of the cam shaft 112 in the direction of R1. Similarly, movement of the gear rack 166 in the direction of arrow L2 induces motion of the cam shaft in the direction of arrow R2.

The plunger assembly 116 engages the cam shaft 112 as the cam shaft 112 rotates. The plunger assembly 116 includes a knob support plate 172 fixedly coupled to the frame 110 with screws 174. The knob support plate 172 receives a spring-loaded plunger screw 176. The plunger screw 176 is positioned such that a head 180 of the plunger screw 176 engages a drum member 120 along the cam surface 122 as the cam shaft 112 rotates freely in the direction of arrow R1 or R2. As the plunger screw 176 encounters the slot 126 of the drum member 120, however, the head 180 extends into the slot 126 to prevent further rotational motion of the cam shaft 112.

Figure 5A:
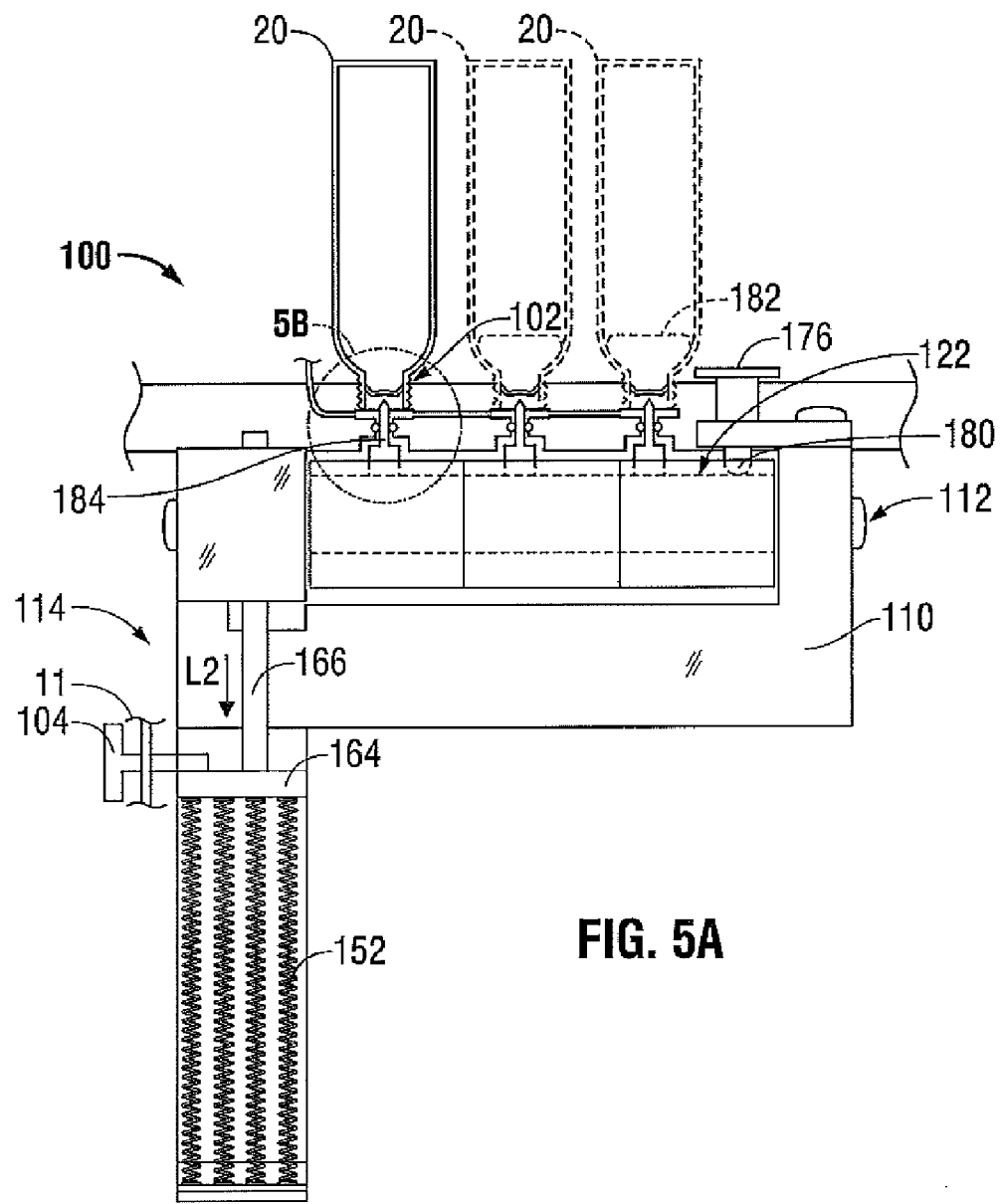
FIG. 5A is a schematic view of the gas cylinder and puncture assembly in a pre-set configuration wherein the gas cylinder is sealed.

Referring now to FIG. 5A, the puncture assembly 100 may be moved to a pre-set configuration wherein the springs 152 are in a compressed state and store energy. The gear rack 166 and second L-bracket 164 are moved in the direction of arrow L2 to a pre-set position. Release pin 104 engages the second L-bracket 164 to prevent motion of the drive assembly 114. The head 180 of the plunger screw 176 engages the cam surface 122 of one of the drum members 120.

Figure 5B:
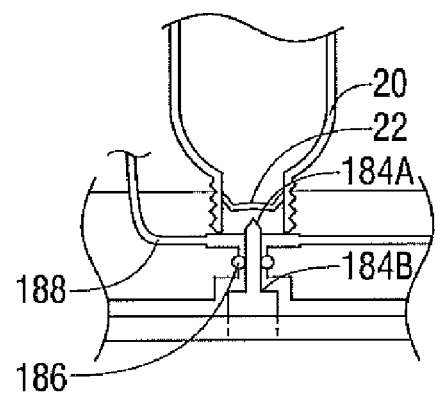
FIG. 5B is an enlarged view of the area of detail identified in FIG. 5A.

At least one cylinder 20 is screwed into the port 102 approximate the cam shaft 112. Multiple ports 182 may be provided to accommodate embodiments wherein multiple cylinders 20 are to be punctured. A plug 182 may be provided to prevent gas leakage through any un-used port 102. A puncture pin 184 is disposed within the poll 102. As depicted in FIG. 5B, the puncture pin 184 includes a sharpened tip portion 184a and a head portion 184b extending out of the port 102. The sharpened tip portion 184a is disposed toward the rupture disk seal 22 and forms a radial seal with an o-ring 186 or similar component. The o-ring 186 inhibits leakage of any surgical gas released from cylinder 20 from a passageway 188 leading to plenum 26 (FIG. 1A) or gas supply hose 80 (FIG. 2). The head portion 184b of the puncture pin 184 engages the cam surface 122 of one of the drum members 120. The drum members 120 are positioned such that the head portion 184b engages the cam surface 122 at a location where the radius of the drum member is at a minimum. A biasing member (not shown) may be provided such that the head portion 184b maintains contact with the cylinder 120 as the cam shaft 112 rotates.

Figure 6A:
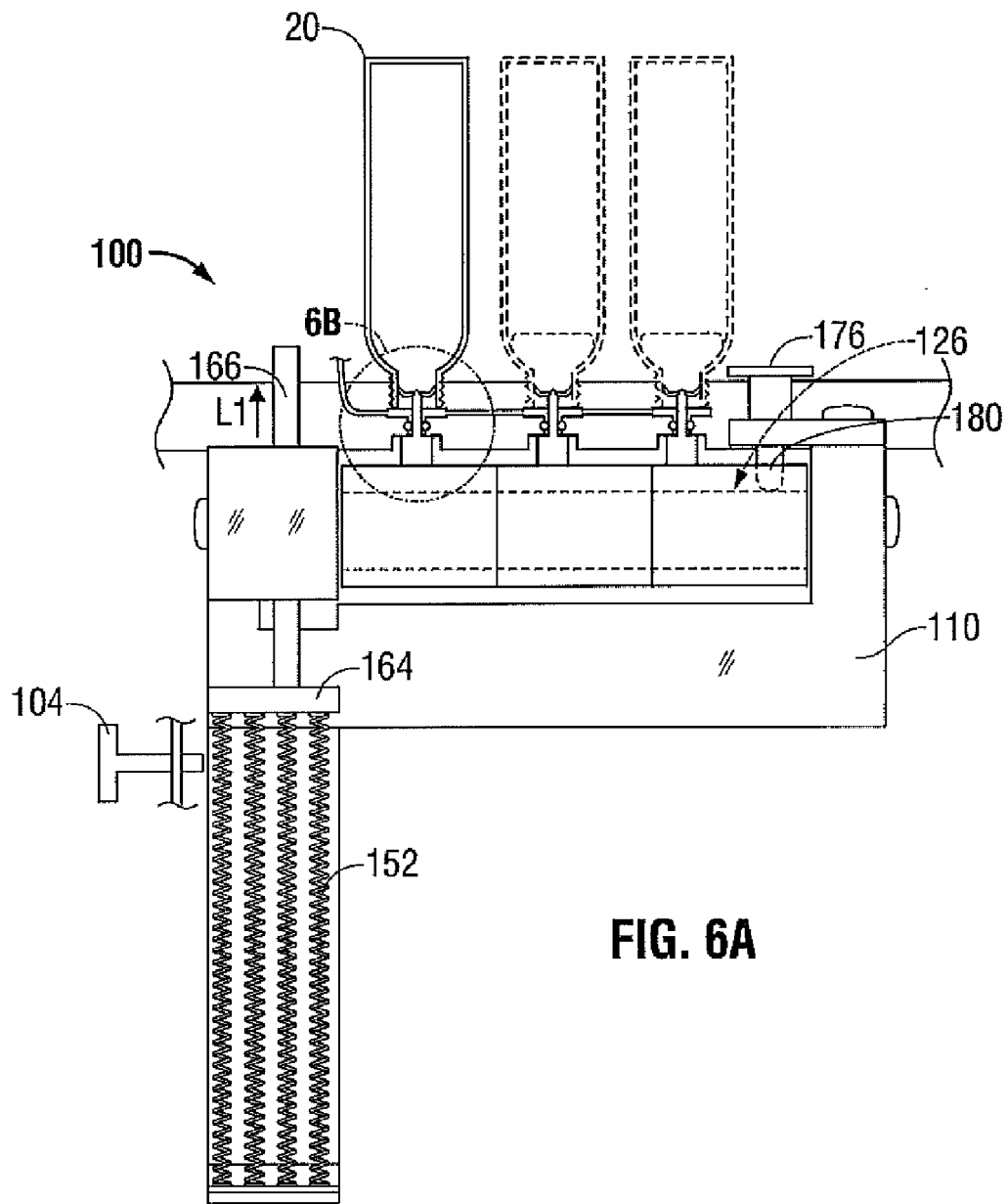
FIG. 6A is a schematic view of the gas cylinder and puncture assembly in an actuated configuration wherein the gas cylinder is ruptured.
Figure 6B:
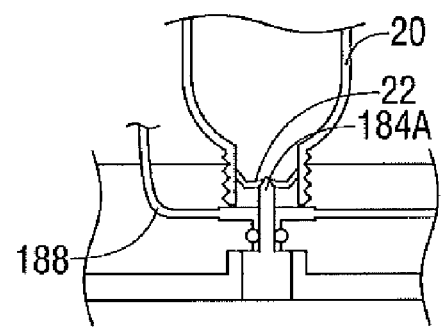
FIG. 6B is an enlarged view of the area of detail identified in FIG. 6A.

Referring now to FIGS. 6A and 6B, the puncture assembly 100 may be actuated to puncture the rupture disk seal 22. The release pin 104 is moved to an actuated position wherein the release pin 104 is disengaged from the second L-bracket 164.

The energy stored in springs 152 is thereby released, driving the second L-bracket 164 and the gear rack 166 in the direction of arrow L1. The motion of the gear rack 166 causes the pinion gear 134 (FIG. 3) and cam shaft 112 to rotate in the direction of arrow R1 (FIG. 4). The cam surfaces 122 of the drum members 120 drive the puncture pin 184 toward the cylinder 20. The springs 152 impart a sufficient torque to the cam shaft 112 to drive the tip portion 184a through the rupture disk seal 22. Surgical gas is then released from the cylinder 20 into the passageway 188 leading toward the plenum 26 (FIG. 1A) or gas supply hose 80 (FIG. 2). The head 180 of plunger screw 176 engages the slot 126 in one of the drum members 120 to prevent any over-travel of the cam shaft 112.

In this manner, an operator may puncture the cylinder 20 with a relatively small input force imparted to the release pin 104. The input force is sufficient to actuate the springs 152, but not necessarily sufficient alone to drive puncture pin 184 through the rupture disk seal 22. This arrangement may facilitate operation of an electrosurgical instrument 10 (FIG. 1A) during a surgical procedure.

To reset the puncture assembly 100 once the release pin 104 is removed, the springs 152 may be compressed, and the release pin 104 may be replaced at a convenient time prior to further surgical procedures. In some embodiments, the user may have access to the mechanisms required to reset the puncture assembly 100. In other embodiments, the user may be effectively locked out, thus requiring the instrument 10 to be rebuilt or refurbished by the manufacturer in order to reset the puncture assembly 100.

The number of springs 152 or the spring constant of the springs 152 may be varied to configure the puncture assembly 100 to store a sufficient amount of energy to puncture a particular type of cylinder or cylinders 20. Additionally, the pitch of the gear rack 166 and pinion gear 134 may be varied to accommodate the various puncture forces that may be required.

Figure 7:
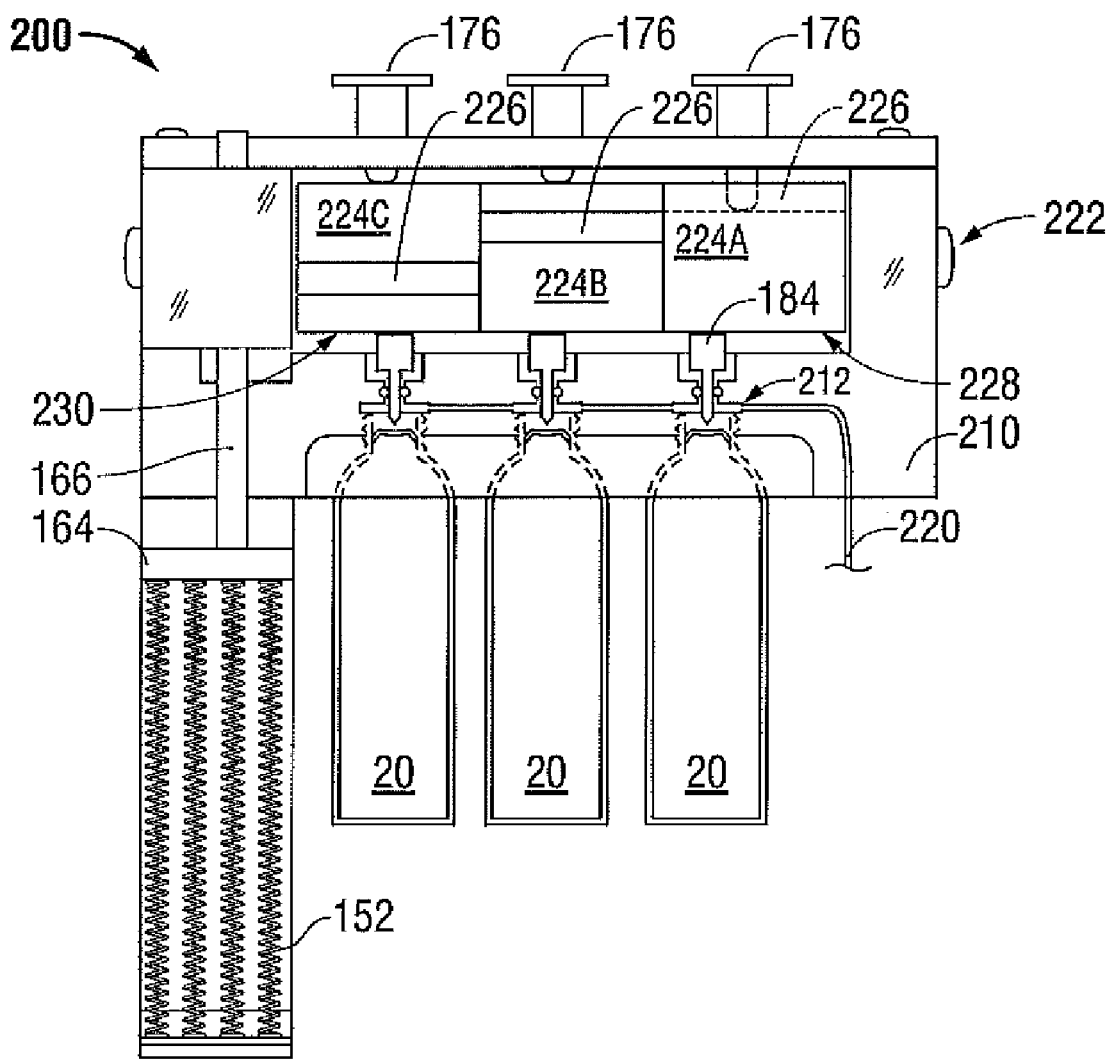
FIG. 7 is a schematic view of an alternate embodiment of a puncture assembly for sequentially rupturing a plurality of cylinders.

Referring now to FIG. 7, an alternate embodiment of a puncture assembly is depicted generally as 200. Puncture assembly 200 is configured to sequentially puncture a series of cylinders 20. The cylinders 20 are screwed into a frame 210 having ports 212 similar to ports 102 described above with reference to FIG. 5B. The ports 212 are in fluid communication with a passageway 220 leading toward the plenum 26 (FIG. 1A) or gas supply hose 80 (FIG. 2), and puncture pins 184 are disposed within the ports 212. A bank of springs 152 is provided to store energy for driving gear rack 166 in a longitudinal direction as described above with reference to FIG. 6. Longitudinal motion of the gear rack 166 induces rotational motion of a cam shaft 222 by engaging a pinion gear (not shown) similarly configured and positioned as the pinion gear 134 described above with reference to FIG. 4.

The cam shaft 222 includes three drum members 224A, 224B and 224C. Each drum member 224A, 224B and 224C includes a slot 226 defined therein, a cam surface 228 and a neutral surface 230. The three drum members 224A, 224B and 224C are configured to rotate together, but are oriented with a radial offset with respect to the neighboring drum members 224A, 224B and 224C. When the puncture assembly 200 is in a pre-set configuration, a first plunger screw 176 engages the slot 226 of drum member 224A, and a respective puncture pin 184 engages the cam surface 228 of the drum member 224A. The engagement of the first plunger screw 176 with the slot 226 prevents rotation of the cam shaft 222 under the influence of the energy stored in springs 152. Due to the radial offset of drum members 224B and 224C, respective plunger screws 176 and puncture pins 184 engage the neutral surfaces 230 of drum members 224B and 224C when the puncture assembly 220 is in the preset configuration.

A first cylinder 20 may be punctured by disengaging the plunger screw 176 from the slot 226 defined in drum member 224A. Disengagement of the plunger screw 176 permits rotation of the cam shaft 222 under the influence of the energy stored in springs 152. The cam surface 228 of drum member 224A drives the respective puncture pin 184 into the corresponding cylinder 20 to release the surgical gas therefrom. The drum members 224B and 224C engage respective puncture pins 184 along neutral surfaces 230 such that the respective puncture pins 184 do not travel toward or puncture corresponding cylinders 20.

The cam shaft 222 continues to rotate until the slot 226 defined in drum member 224B encounters a respective plunger screw 176. The plunger screw 176 then engages the slot 226 defined in drum member 224B and prevents further rotation of the cam shaft 222. The remaining energy stored in springs 152 is sufficient to puncture additional cylinders 20. As the plunger screw 176 is engaged with the slot 226 defined in drum member 224B, the cam surface 228 of drum member 224B is positioned such that further rotation of the cam shaft 222 drives the respective puncture pin 184 toward the corresponding cylinder 20. Thus by sequentially disengaging the plunger screws 176 from the slots 226 defined in drum members 224A, 224B and 224C, a plurality of cylinders 20 may be sequentially ruptured.

Figure 8A:
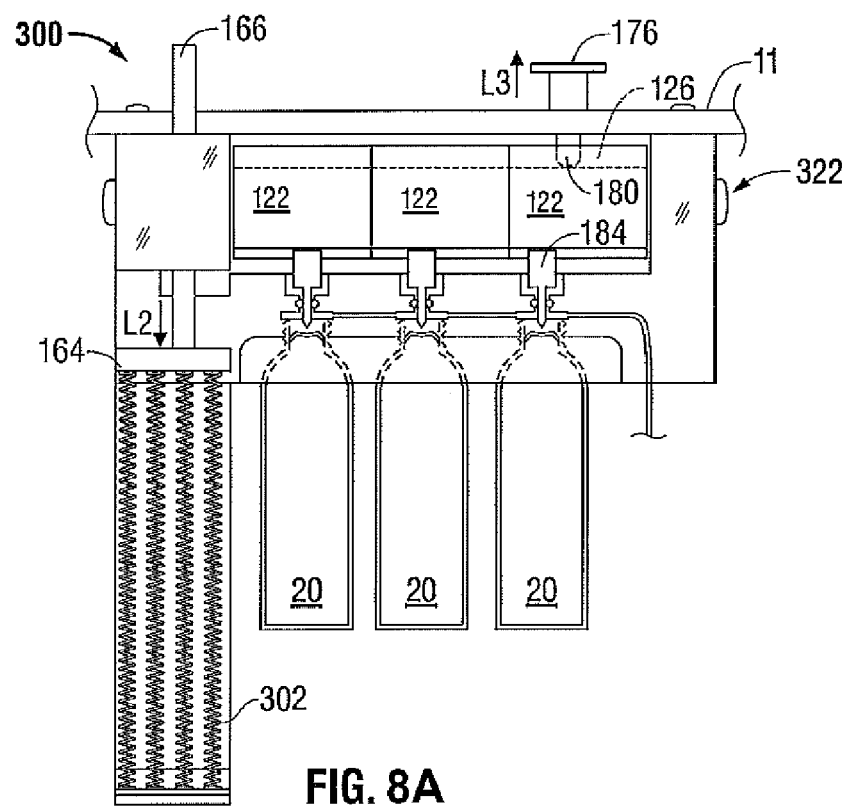
FIG. 8A is a schematic view of an alternate embodiment of a puncture assembly in a pre-set configuration wherein a hank of extension springs are in a first state for storing energy.

Referring now to FIG. 8A, an alternate embodiment of a puncture assembly 300 is depicted in a pre-set configuration. Puncture assembly 300 includes a bank of extension springs 302 configured to store energy in first tensile state. The springs 302 are provided in a stretched configuration such that sufficient energy is stored in the springs 302 to drive cam shaft 322 and puncture cylinder or cylinders 20.

In the pre-set configuration, springs 302 exert a force on the L-bracket 164 in the direction of arrow L2. As in the embodiment described above with reference to FIG. 3, the L-bracket 164 is fixedly coupled to gear rack 166, and the gear rack 166 engages pinion gear 134 (FIG. 3) of cam shaft 322. Thus, the force exerted by the springs 302 is transmitted to the cam shaft 322. The cam shaft 322 is prevented from rotating under the influence of this force by the head 180 of plunger screw 176 extending into the longitudinal slot 126. An end opposite the head 180 of the plunger screw 176 extends to an exterior of housing 11 such that the plunger screw 176 is accessible to a user during a coagulation procedure. The user may manipulate the plunger screw 176 to draw the head 180 from the slot 126 in the direction of arrow L3, and thereby permit the cam shaft 322 to rotate under the influence of the springs 302. Thus, puncture assembly 300 is actuated by manipulating the plunger screw 176.

Figure 8B:
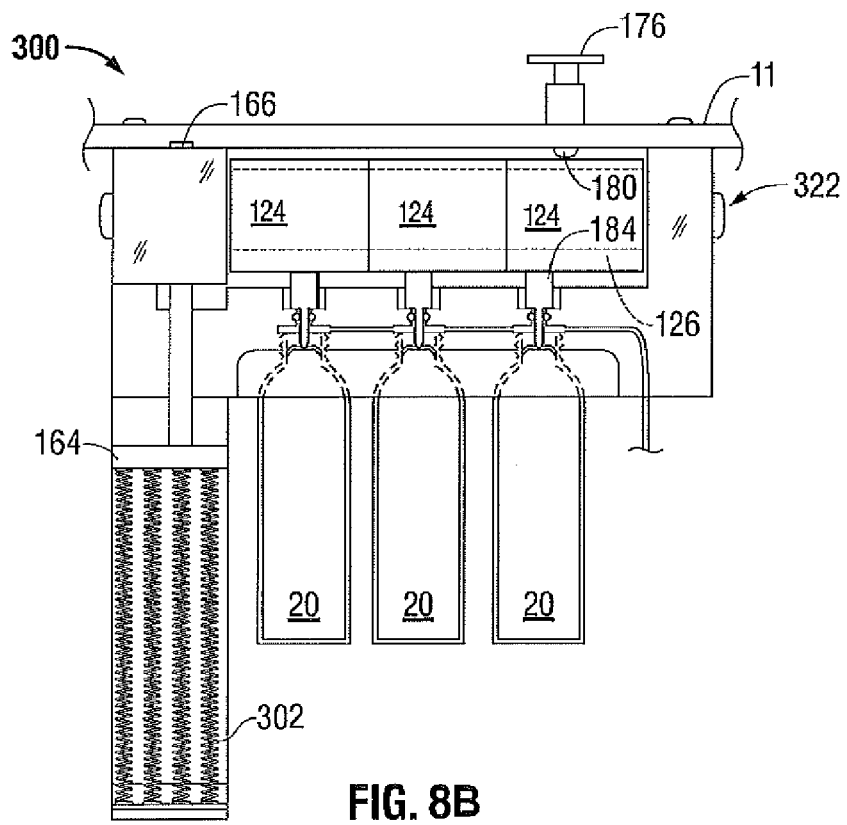
FIG. 8B is a schematic view of the puncture assembly of FIG. 8A in an actuated configuration wherein the extension springs are in a relaxed state.

Upon actuation of the puncture assembly 300, the puncture assembly 300 moves from the pre-set configuration depicted in FIG. 8A to an actuated configuration depicted in FIG. 8B. The springs 302 move to a relaxed state drawing L-Bracket 164 and gear rack 166 in the direction of arrow L2. The longitudinal motion of the gear rack 166 induces rotational motion in the cam shaft 322 such that the orientation of the cam surfaces 122 and neutral surfaces 124 are reversed. The cam surfaces 124 engage the puncture pins 184 as the cam shaft 322 rotates, and the puncture pins 184 are driven toward the cylinders 20. Thus, the cylinders 20 are punctured when the user manipulates the plunger screw 176. Puncture assembly 300 permits a user to puncture cylinders 20 by providing only a force sufficient to remove the head 180 from the slot 126. This arrangement may prove to be a viable alternative to directly puncturing the cylinders 20.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument for providing a gas to a surgical site, comprising:
    a receptacle for receiving at least one cylinder of pressurized surgical gas;
    a frame having a proximal end and a distal end, the frame defining a port near the distal end for emitting the surgical gas;
    an electrode disposed adjacent the distal end of the frame, the electrode adapted for connection to a source of electrosurgical energy;
    a passageway extending between the receptacle and the port defined in the frame, the passageway for delivering the surgical gas to the electrode; and
    a puncture assembly for rupturing a seal defined by a cylinder to release the surgical gas into the passageway, the puncture assembly comprising:
        at least one spring movable between a first state for storing mechanical energy and a relaxed state;
        an actuator operable to move the spring to the relaxed state;
        at least one puncture pin operatively coupled to the spring such that the mechanical energy released by movement of the spring to the relaxed state is effective to move the puncture pin relative to a cylinder to rupture the seal; and
    a gear rack and a pinion gear, wherein the puncture pin is operatively coupled to the spring via the gear rack and the pinion gear such that movement of the spring to the relaxed state induces longitudinal motion in the gear rack, and the longitudinal motion in the gear rack induces rotational motion in the pinion gear.

2. The surgical instrument according to claim 1, further comprising a cam shaft, wherein the pinion gear is operatively coupled to the cam shaft, and wherein rotational motion in the cam shaft induces longitudinal motion between the puncture pin and a cylinder.

3. The surgical instrument according to claim 2, wherein the actuator includes a plunger configured to engage a slot in the cam shaft such that disengaging the plunger from the slot induces movement of the spring to the relaxed state.

4. The surgical instrument according to claim 2, wherein the at least one puncture pin includes a plurality of puncture pins and wherein the receptacle is configured to receive a plurality of cylinders, and wherein the cam shaft operatively engages a the plurality of puncture pins such that each of the plurality of puncture pins is movable relative to a respective cylinder.

5. The surgical instrument according to claim 1, wherein the at least one puncture pin includes a plurality of puncture pins and wherein the receptacle is configured to receive a plurality of cylinders, and wherein the puncture assembly includes the plurality of puncture pins each movable simultaneously with respect to one another relative to the plurality of cylinders such that each of the plurality of cylinders may be punctured simultaneously.

6. The surgical instrument according to claim 1, wherein the at least one puncture pin includes a plurality of puncture pins and wherein the receptacle is configured to receive a plurality of cylinders, and wherein the puncture assembly includes the plurality of puncture pins each movable sequentially with respect to one another relative to a respective cylinder such that each of the plurality of cylinders may be punctured sequentially.

7. The surgical instrument according to claim 1, wherein the at least one spring includes a compression spring such that the compression spring is subject to a compressive force in the first state.

8. The surgical instrument according to claim 1, wherein the at least one spring includes an extension spring such that the extension spring is subject to a tensile force when in the first state.

9. The surgical instrument according to claim 1, wherein the receptacle is disposed within the frame.

10. The surgical instrument according to claim 1, wherein the receptacle is disposed remotely with respect to the frame, and wherein the passageway includes a gas supply hose.

11. The surgical instrument according to claim 1, wherein a source of electrosurgical energy is disposed within the frame.

12. The surgical instrument according to claim 1, wherein a source of electrosurgical energy is disposed remotely with respect to the frame and coupled to the frame by a cable.

13. A surgical instrument for providing a gas to a surgical site, comprising:
   a receptacle for receiving at least one cylinder of pressurized surgical gas;
   a frame having a proximal end and a distal end, the frame defining a port near the distal end for emitting the surgical gas;
   an electrode disposed adjacent the distal end of the frame, the electrode adapted for connection to a source of electrosurgical energy;
   a passageway extending between the receptacle and the port defined in the frame, the passageway for delivering the surgical gas to the electrode; and
   a puncture assembly for rupturing a seal defined by a cylinder to release the surgical gas into the passageway, the puncture assembly comprising:
      at least one spring movable between a first state for storing mechanical energy and a relaxed state;
      an actuator operable to move the spring to the relaxed state;
      a plurality of puncture pins operatively coupled to the spring such that the mechanical energy released by movement of the spring to the relaxed state is effective to move the puncture pin relative to a cylinder to rupture the seal; and
   a cam shaft, wherein the movement of the spring to the relaxed state induces rotational motion in the cam shaft, the cam shaft including a plurality of cam surfaces radially offset from one another, and wherein each of the plurality of cam surfaces operatively engages at least one of the plurality of puncture pins,
   wherein the receptacle is configured to receive a plurality of cylinders, and wherein the puncture assembly includes the plurality of puncture pins each movable sequentially with respect to one another relative to a respective cylinder such that each of the plurality of cylinders may be punctured sequentially.

* * * * *